US00PP14199P29

(12) United States Plant Patent
Lounsbury et al.

(10) Patent No.: US PP14,199 P2
(45) Date of Patent: Oct. 7, 2003

(54) ANTHURIUM PLANT NAMED 'WHITE GIMINI'

(50) Latin Name: *Aglaonema X hybrid*
Varietal Denomination: White Gemini

(75) Inventors: Milton Lounsbury, Homestead, FL (US); David R. Lilly, Boynton Beach, FL (US)

(73) Assignee: Twyford International, Inc., Santa Paula, CA (US)

( * ) Notice: Subject to any disclaimer, the term of this patent is extended or adjusted under 35 U.S.C. 154(b) by 0 days.

(21) Appl. No.: 10/171,948

(22) Filed: Jun. 17, 2002

(51) Int. Cl.[7] ..... A01H 5/00
(52) U.S. Cl. ..... Plt./366
(58) Field of Search ..... Plt./366

*Primary Examiner*—Bruce R. Campell
*Assistant Examiner*—Annette H. Para
(74) *Attorney, Agent, or Firm*—C. A. Whealy

(57) ABSTRACT

A distinct cultivar of Anthurium plant named 'White Gemini', characterized by its upright and outwardly spreading plant habit; shiny dark green leaves; white-colored spathes with white and yellow green spadices; inflorescences that are positioned above and beyond the foliage on strong and erect scapes; and excellent inflorescence longevity.

1 Drawing Sheet

Botanical classification/cultivar designation: Aglaonema× hybrid cultivar White Gemini.

BACKGROUND OF THE INVENTION

The present invention relates to a new and distinct cultivar of Anthurium plant, botanically known as Anthurium× hybrid, and hereinafter referred to by the name 'White Gemini'.

The new Anthurium is a naturally-occurring whole plant mutation of the Anthurium×hybrid cultivar Gemini, disclosed in U.S. Plant Pat. No. 10,043. The new Anthurium was discovered by the Inventors in a controlled environment in Princeton, Fla., as a single plant within a group of tissue culture-derived plants of 'Gemini' on or about Dec. 8, 1998. The selection of this plant was based on its white-colored spathes.

Asexual propagation of the new cultivar by meristem culture in a controlled environment in Sebring, Fla., since December, 1998, has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature, daylength and light intensity, without, however, any variance in genotype.

The following traits have been repeatedly observed and are determined to be the unique characteristics of the cultivar White Gemini. These characteristics in combination distinguish 'White Gemini' as a new and distinct cultivar:

1. Upright and outwardly spreading plant habit.
2. Shiny dark green leaves.
3. White-colored spathes with white and yellow green spadices.

4. Inflorescences that are positioned above and beyond the foliage on strong and erect scapes.
5. Excellent inflorescence longevity.

Plants of the new Anthurium differ from plants of the cultivar Gemini primarily in spathe coloration as plants of the cultivar Gemini have pink-colored spathes.

Plants of the new Anthurium can be compared to plants of the cultivar Peppermint Gemini, U.S. Plant patent application Ser. No. 10/171,836 filed concurrently with this application. In side-by-side comparisons conducted in Sebring, Fla., plants of the new Anthurium differed from plants of the cultivar Peppermint Gemini primarily in spathe coloration as plants of the cultivar Peppermint Gemini had white and pink mottled spathes.

BRIEF DESCRIPTION OF THE PHOTOGRAPHS

The accompanying colored photographs illustrate the overall appearance of the new Anthurium, showing the colors as true as it is reasonably possible to obtain in colored reproductions of this type. Colors in the photographs may differ slightly from the color values cited in the detailed botanical description which accurately describe the colors of the new Anthurium.

The photograph at the top of the sheet comprises a side perspective view of a typical flowering plant of the cultivar White Gemini grown in a container.

The photograph at the bottom of the sheet comprises a side-by-side comparison of plants of the cultivar Gemini (left) and White Gemini (right).

DETAILED BOTANICAL DESCRIPTION

The aforementioned photographs and the following observations and measurements describe 9-month old plants grown in containers in Homestead, Fla., in a polypropylene-covered shadehouse with day temperatures of 21 to 32° C., night temperatures of 18 to 24° C., and light levels about 1,500 foot-candles.

In the following description, color references are made to The Royal Horticultural Society Colour Chart except where general terms of ordinary dictionary significance are used.

Botanical classification: *Anthurium andreanum* cultivar White Gemini.

Parentage: Naturally-occurring whole plant mutation of Anthurium×hybrid cultivar Gemini, disclosed in U.S. Plant Pat. No. 10,043.

Propagation:

*Method.*—By meristem culture.

*Time to initiate roots on a meristem-cultured plant.*—About 10 days at day temperatures of 21 to 32° C. and night temperatures of 18 to 24° C.

*Time to develop roots on a meristem-cultured plant.*—About 147 days at day temperatures of 21 to 32° C. and night temperatures of 18 to 24° C.

*Root description.*—Strong fleshy roots with fine lateral roots; root tip, 145B in color.

Plant description:

*Plant shape.*—Upright and outwardly spreading plant habit, inverted triangle, symmetrical.

*Growth habit.*—Freely clumping, bushy and dense growth habit.

*Plant height.*—About 22 to 26 cm.

*Plant diameter or spread.*—About 37 to 48 cm.

*Crop time.*—About 9 months are usually required from planting of young plants to finished flowering plants in a 15-cm container.

*Foliage description.*—Length: About 17.1 to 19.8 cm. Width: About 8 to 10.5 cm. Shape: Ovate to broadly lanceolate. Apex: Acute, tapered. Base: Obtuse to truncate; base has two rounded lobes that do not extend past the petiole junction. Margin: Entire; slightly undulate. Texture: Leathery; glabrous. Venation: Midvein with well-defined primary veins radiating out from the petiole junction. Midvein protrudes from the upper surface for about 75% of the leaf length. Primary veins are sunken on the upper surface and protrude on the lower surface. Petiole: Length: About 9.2 to 11.1 cm. Diameter, just below the geniculum: About 4 mm. Geniculum: Length: About 2.5 to 3 cm. Diameter: About 4.5 mm. Orientation: Curved or bent. Petiole sheath: Length: About 6 mm. Width, at midpoint: About 3 mm. Distance from apex of petiole sheath to base of geniculum: About 7.5 to 9.1 cm. Apex: Rounded. Cataphyll: New leaves emerge from a cataphyll which turns brown, 200C, with subsequent development and eventually abscises. Length: About 7 to 10 cm. Width, at base: About 2 to 2.3 cm. Shape: Triangular. Apex: Apiculate. Margin: Entire. Texture, upper and lower surfaces: Smooth. Color: Upper leaf surface: Closest to, but much darker and more green than 147A; shiny. Lower leaf surface: 146B. Midrib, upper surface: 146B. Midrib, lower surface: 145A. Petiole: 144A to 146B. Geniculum: 146B to 146C. Petiole sheath: 144A to 146C. Cataphyll, upper surface: 145C to 145D. Cataphyll, lower surface: 146D; glossy.

Inflorescence description:

*Inflorescence arrangement.*—When developing, the spathe is tightly rolled around the spadix and emerges from the petiole sheath. The spathe is fully opened approximately when the peduncle is fully elongated. Spathes with spadices held above and beyond the foliage on straight wiry peduncles and open vertically. Inflorescences are typically grouped in the center of the plant. Freely and continuous flowering year-round; about 4 to 6 open inflorescences and about 3 flower buds per plant at one time.

*Inflorescence longevity.*—Inflorescences maintain good color and substance on the plant for about 8 weeks. As cut flowers, inflorescences maintain good color and substance for about 2 to 3 weeks. Inflorescences persistent.

*Time to flower.*—First flowers develop about 7 months after planting 20-week old rooted plants.

*Spathe.*—Length: About 5.5 to 6 cm. Width: About 4 to 4.3 cm. Shape: Ovate. Apex: Cuspidate, hooked upward. Base: Cordate to truncate. Margin: Entire. Texture: Leathery; glabrous. Aspect: Initially cupped, flattening with development. Color: Fully opened, front surface: White; brighter than, but closest to 155D. Fully opened, back surface: White, 155D. Faded, front and back surfaces: White, 155D, with random green, 144A, spots.

*Spadix.*—Length: About 3.1 to 3.4 cm. Diameter: About 6 mm. Shape: Columnar. Cross section: Rounded. Longitudinal axis: Erect. Color: When the spathe unrolls, the spadix is lighter than but closest to 159D, becoming 160A at the apex. The spadix becomes yellow, 160A, and green, 146B, mottled with development.

*Reproductive organs.*—Androecium: Anthers and filaments are minute and not clearly visible. Pollen color: White, close to 155D. Gynoecium: Pistils are translucent white and protrude between the staminate flowers and extend about 0.5 mm beyond the stamens.

*Scape.*—Length: About 32 to 40 cm. Aspect: Strong and erect, wiry. Color: 144A to 146B.

*Seed/fruit.*—Seed/fruit development on plants of the new Anthurium has not been observed.

Disease/pest resistance: Under commercial conditions, plants of the new Anthurium have not been observed to be resistant to pathogens or pests common to Anthurium.

Temperature tolerance: Plants of the new Anthurium have been observed to be tolerant to temperatures ranging from 7 to 40° C.

It is claimed:

1. A new and distinct cultivar of Anthurium plant named 'White Gemini', as illustrated and described.

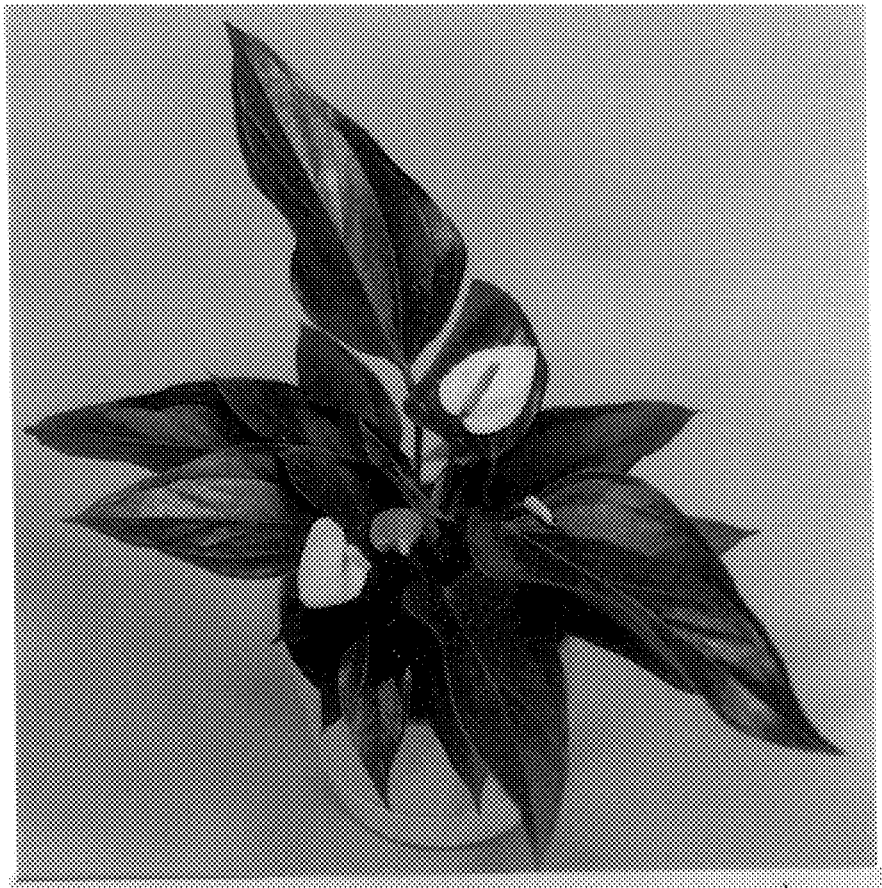
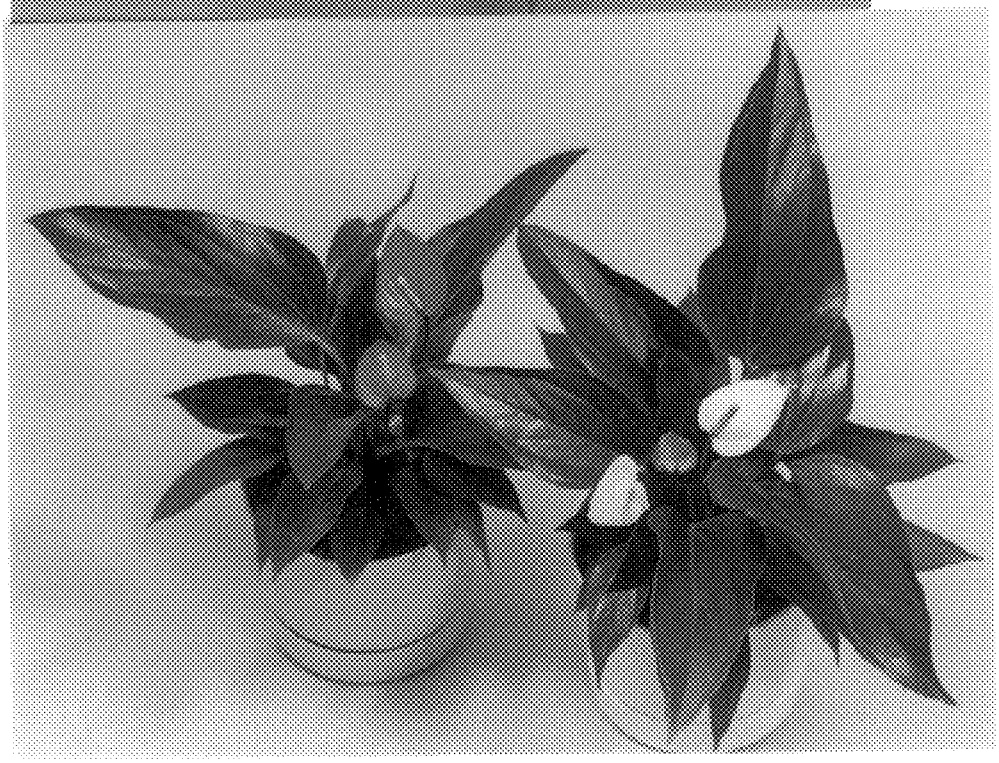

* * * * *